(12) United States Patent
Greenberg

(10) Patent No.: US 8,936,605 B2
(45) Date of Patent: Jan. 20, 2015

(54) DIRECT VERTEBRAL ROTATION TOOL AND METHOD OF USING SAME

(75) Inventor: Daniel Greenberg, Ramsey, NJ (US)

(73) Assignee: Blackstone Medical, Inc., Lewisville, TX (US)

( * ) Notice: Subject to any disclaimer, the term of this patent is extended or adjusted under 35 U.S.C. 154(b) by 19 days.

(21) Appl. No.: 13/341,599

(22) Filed: Dec. 30, 2011

(65) Prior Publication Data
US 2013/0172947 A1 Jul. 4, 2013

(51) Int. Cl.
*A61B 17/70* (2006.01)
(52) U.S. Cl.
USPC .................... 606/104; 606/99; 606/86 A
(58) Field of Classification Search
USPC .............. 606/250–279, 86 A, 99, 190–194
See application file for complete search history.

(56) References Cited

U.S. PATENT DOCUMENTS

| | | |
|---|---|---|
| 5,281,223 A | 1/1994 | Ray |
| 5,385,565 A | 1/1995 | Ray |
| 2002/0052603 A1 | 5/2002 | Nichols et al. |
| 2005/0033291 A1 | 2/2005 | Ebara |
| 2006/0111712 A1 | 5/2006 | Jackson |
| 2006/0149236 A1 | 7/2006 | Barry |
| 2006/0195092 A1 | 8/2006 | Barry |
| 2007/0288012 A1* | 12/2007 | Colleran et al. ............... 606/61 |
| 2008/0294206 A1 | 11/2008 | Choi et al. |
| 2011/0172714 A1* | 7/2011 | Boachie-Adjei et al. ..... 606/264 |
| 2011/0313460 A1* | 12/2011 | McLean et al. ............... 606/264 |

OTHER PUBLICATIONS

International Search Report and Written Opinion, PCT/US2012/072105, 10 pages, dated Mar. 8, 2013.

* cited by examiner

*Primary Examiner* — Mary Hoffman
*Assistant Examiner* — Tara Carter
(74) *Attorney, Agent, or Firm* — Baker & McKenzie LLP

(57) ABSTRACT

A head holder for holding and tensioning the head of a bone screw, particularly a pedicle screw, is provided. Also provided is a ratcheting connector for connecting to the head holders while permitting rotational movement of the head holder when engaged with the ratcheting connector. Also provided is a flex arm connector for connecting multiple ratcheting connectors across multiple vertebral bodies. A tool set for managing and/or correcting spinal deformities, such as scoliosis, including at least one or more head holders and one or more ratcheting connectors is provided.

20 Claims, 6 Drawing Sheets

DIRECT VERTEBRAL ROTATION TOOL AND METHOD OF USING SAME

BACKGROUND

The present invention relates to tools and methods for use in performing spinal surgery and, in particular, to tools and methods of using such tools, especially for management and correction of spinal deformities, such as scoliosis.

Spinal osteosynthesis apparatuses have been utilized to correct spinal deformities, injuries or disease for many years. After the implantation of pedicle screws, a spinal surgeon may insert a metal rod to join a series of vertebral bodies, creating a stable construct and promoting biological fusion of the spinal column. This technique is common for small-level (i.e., "short-construct") degenerative spinal procedures, as well as multi-level (i.e., "long-construct") deformity procedures. Spinal deformities often consist of sagittal or coronal curvature, combined with a rotational component along the axis of the spine. Rotational components of a spinal deformity have been addressed using a technique called Direct Vertebral Body Rotation (DVR). However, the tools and methods currently employed in DVR provide challenges. Many such known systems are very technique-dependent and time consuming to implement. It is desirable, therefore, to have a simple-to-use system that produces effective correction of the rotational component of the spinal deformity.

SUMMARY

One aspect of this disclosure relates to a head holder, including a handle portion having generally tubular shape, a distal end and a proximal end; an inner sheath having a tubular proximal end and a distal end having two U-shaped cutouts, two arc-shaped head clamp portions, and one or more pins; and an outer sheath having a distal end and a proximal ring section, the proximal ring section including a locking mechanism which permits the outer sheath to move between and to reside in locked and unlocked positions; wherein the proximal end of the inner sheath is attached to the handle portion, the outer sheath surrounds the inner sheath, a spring surrounds the inner sheath and rests between a distal edge of the handle portion and a proximal edge of the outer sheath. The locking mechanism of the proximal ring section may comprise a locking ring, a set spring, and a locking button. The distal end of the outer sheath may also comprises two opposing U-shaped cutouts for receiving a rod.

Another aspect of this disclosure relates to a ratcheting connector that includes a first arm comprising an inner section and an outer section, the outer section comprising a first adjustable circular sleeve; a first rotatable bearing rotatably mounted within the first adjustable sleeve; a mechanism to lock the first adjustable circular sleeve around the first rotatable bearing; a second arm comprising an inner section, an outer section, the outer section comprising a second adjustable circular sleeve, and a receptacle having an opening; a second rotatable bearing rotatably mounted within the second adjustable sleeve; a mechanism to lock the second adjustable circular sleeve around the second rotatable bearing; wherein the inner sections of the first and second arms lockably interconnect to permit adjustment of the distance between the first and second circular openings.

A flex arm connector may be utilized that includes a plurality of nesting cups, each cup having a female portion and a male portion such that a male portion fits within a female portion, the plurality of nesting cups forming a flexible length; a mechanism for locking the flex arm connector into a desired configuration attached to one end of the flexible length; and one or more adjustable sleeves slidably mounted on the flexible length, each sleeve further including a swivel post configured to interlock with a rotation handle receptacle. The adjustable sleeve of the flex arm connector may further comprise a receptacle having an opening, the receptacle located opposite the swivel post.

A tool set may be utilized to adjust spinal deformities, including one or more head holders that include a handle portion having generally tubular shape, a distal end and a proximal end; an inner sheath having a tubular proximal end and a distal end having two U-shaped cutouts and two arc-shaped head clamp portions; and an outer sheath having a distal end and a proximal ring section, the proximal ring section including a locking mechanism which permits the outer sheath to move between and to reside in locked and unlocked positions; wherein the proximal end of the inner sheath is attached to the handle portion, the outer sheath surrounds the inner sheath, a spring surrounds the inner sheath and rests between a distal edge of the handle portion and a proximal edge of the outer sheath; and one or more ratcheting connectors including a first arm comprising a flat section, and a bent section, the bent section comprising a first adjustable circular sleeve; a first rotatable bearing rotatably mounted within the first adjustable sleeve; a mechanism to lock the first adjustable circular sleeve around the first rotatable bearing; a second arm comprising a flat section, a bent section, the bent section comprising a second adjustable circular sleeve, and a receptacle having an opening; a second rotatable bearing rotatably mounted within the second adjustable sleeve; a mechanism to lock the second adjustable circular sleeve around the second rotatable bearing; wherein the flat sections of the first and second arms interconnect to permit adjustment of the distance between the first and second circular openings.

The tool set may further includes a flex arm connector comprising a plurality of nesting cups, each cup having a female portion and a male portion such that a male portion fits within a female portion, the plurality of nesting cups forming a flexible length; a mechanism for locking the flex arm connector into a desired configuration attached to one end of the flexible length; one or more adjustable sleeves slidably mounted on the flexible length, each sleeve further including a swivel post and rotation handle opening. The tool set may further include one or more rotation handles interconnectable with the rotation handle opening.

A tool set for the adjustment of spinal deformities can be utilized that comprises one or more head holders that include a handle portion having generally tubular shape, a distal end and a proximal end; an inner sheath having a tubular proximal end and a distal end having two U-shaped cutouts and two arc-shaped head clamp portions; and an outer sheath having a distal end and a proximal ring section, the proximal ring section including a locking mechanism which permits the outer sheath to move between and to reside in locked and unlocked positions; wherein the proximal end of the inner sheath is attached to the handle portion, the outer sheath surrounds the inner sheath, a spring surrounds the inner sheath and rests between a distal edge of the handle portion and a proximal edge of the outer sheath; and one or more ratcheting connectors including a first arm comprising a flat section, and a bent section, the bent section comprising a first adjustable circular sleeve; a first rotatable bearing rotatably mounted within the first adjustable sleeve; a mechanism to lock the first adjustable circular sleeve around the first rotatable bearing; a second arm comprising a flat section, a bent section, the bent section comprising a second adjustable circular sleeve, and a receptacle having an opening; a second rotatable bearing rotatably mounted within the second adjustable sleeve; a mechanism to lock the second adjustable circular sleeve around the second rotatable bearing; wherein the flat sections of the first and second arms interconnect to permit adjustment of the distance between the first and second circular openings; a flex arm connector comprising a plurality of nesting cups, each cup having a female portion and a male portion such that a male portion fits within a female portion, the plurality of nesting cups forming a flexible length; a mechanism for locking the flex arm connector into a desired configuration attached to one end of the flexible length; one or more adjustable sleeves slidably mounted on the flexible length, each sleeve further including a swivel post and rotation handle opening; and one or more rotation handles interconnectable with the rotation handle opening.

DRAWINGS

DETAILED DESCRIPTION

Figure 1:
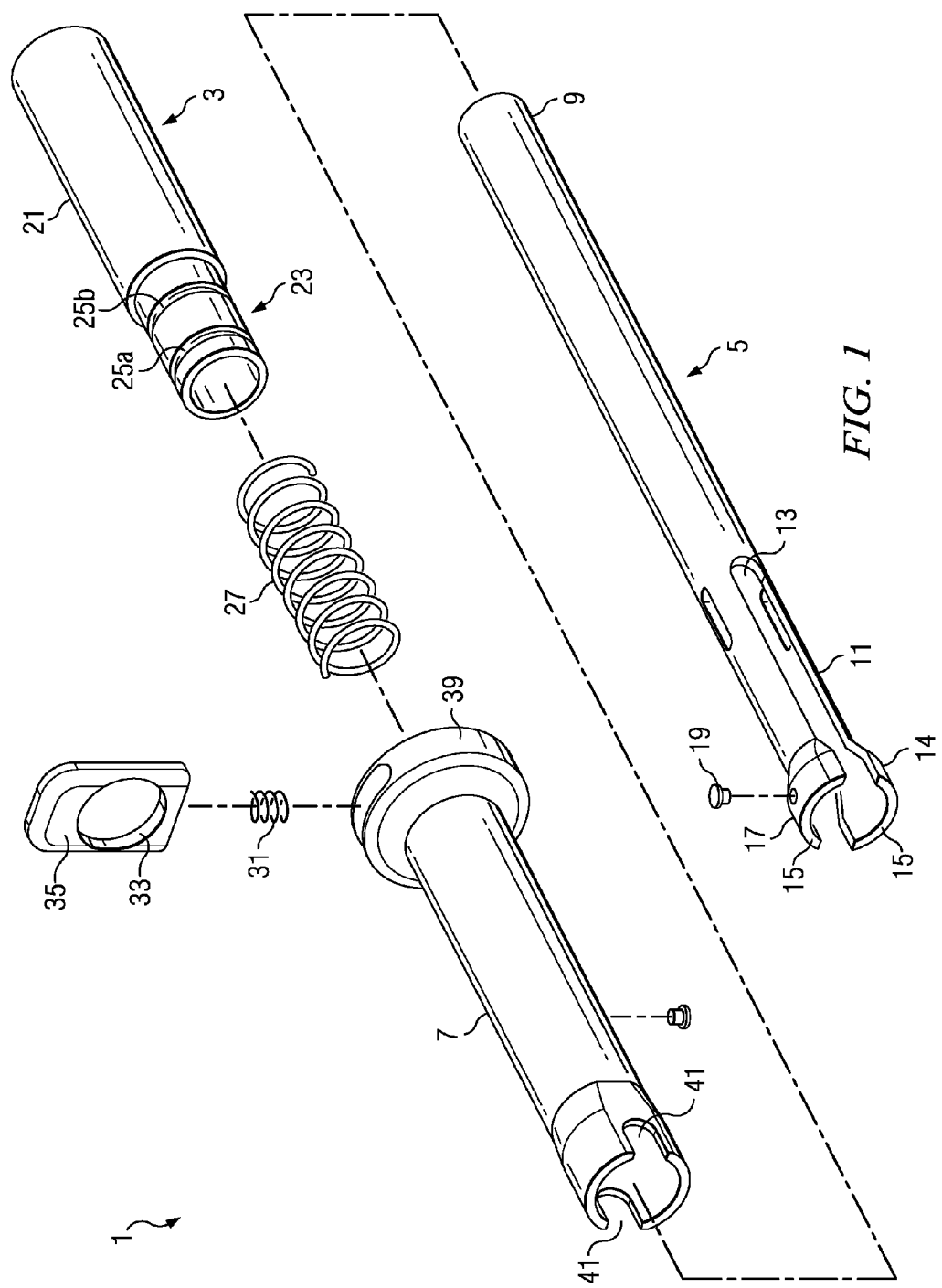
FIG. 1 is an exploded view of an embodiment of a head holder suitable for use with the disclosed invention.

Referring first to FIG. 1, an embodiment of a novel head holder 1 is shown in an exploded view. The head holder includes a handle 3, an inner sheath 5, and an outer sheath 7. Inner sheath 5 may comprise a tubular section 9 that, in the assembled head holder 1, is proximate to the handle 3, and a distal portion 11 configured to grip the head of a bone screw and more particularly, a pedicle screw. As shown, distal portion 11 includes two cutout portions 13 that allow the most distal end of the inner sheath 5 to flex in order to grasp the head of the bone screw. A head clamp portion 14 may be located at the most distal end of inner sheath 5. Head clamp portion 14, as shown in FIG. 1, includes two arc-shaped portions 15. The arc-shaped portions 15 may extend axially outward from the distal portion 11. Each arc-shaped portion 15 may further include an opening 17, through which a pin 19 may be mated. Pin 19 may extend axially into the inner sheath 5. Pin 19 may be configured to mate with or interlock with a spinal implant, such as a pedicle screw.

Referring still to FIG. 1, handle 3 is generally tubular in construction with a proximal portion optionally covered in a comfortable gripping material or surface treatment 21. Handle 3 further includes a distal end 23, that may comprise a tapered or narrower outer diameter than the proximal portion, configured so as to fit within the inside diameter of outer sheath 7. Distal end 23 of handle 3 further includes two grooves 25a and 25b, corresponding to locked and unlocked positions, respectively.

In its assembled configuration, a spring 27 is loaded between outer sheath 7 and handle 3. Inner sheath 5 is then passed into the tubular opening of outer sheath 7, engaging within the tubular opening of handle 3. Outer sheath 7 is maintained in either a locked or unlocked position by locking means. As shown in FIG. 1, the locking means includes a set spring 31, a locking ring 33, and a locking button 35. Outer sheath 7 includes a proximal ring section 39 having an opening through which locking ring 33 passes. Outer sheath 7 further includes a distal portion optionally having U-shaped channels 41 to fit over a rod when head holder 1 is engaged in the locked position on a pedicle screw head.

The head holder 1 provides a secure connection to the head of a pedicle screw and allows for leverage during the surgeon's application of a rotational force. Because the head holder 1 includes a conveniently located and readily operable locking means, the head holder may be used in an initial unlocked position prior to attachment to the pedicle screw head and is easily locked following attachment to the pedicle screw head. Moreover, because of the shape of the head clamp portion 13, the head holder 1 may be connected to a pedicle screw head after the rod has been placed in pedicle screw head.

To utilize the head holder 1, the surgeon sets the outer sleeve to the unlocked configuration, i.e., locking ring 33 is depressed thereby relieving the clumping of outer sheath 7 on inner sheath 5. As the head holder 1 approaches the pedicle screw head, the inner sheath 5 makes contact with the top surface of the pedicle screw head. An axial force is applied along the axis of the head holder 1, causing the inner sheath 5 to open and accept the diameter of the pedicle screw head. The head holder 1 is advanced until the pins 19 make contact with mating features on the pedicle screw head. Once engaged, the locking button 35 is pressed to activate the spring loaded outer sheath 7. The outer sheath 7 is propelled along the axis of the head holder 1 until locked in place around the inner sheath 5. Undercuts 25a and 25b on handle 3 allow the outer sheath 7 to be held in unlocked and locked positions.

In order to disconnect the head holder 1 from a bone screw head, the locking button 35 is pressed and the outer sheath 7 is pulled up the axis of the head holder 1 towards the proximal end of the handle 3 until it reaches the unlocked position. A pulling force is applied along the axis of the head holder 1, allowing the inner sheath 3 to readily and easily separate and disengage from the pedicle screw head.

Figure 2:
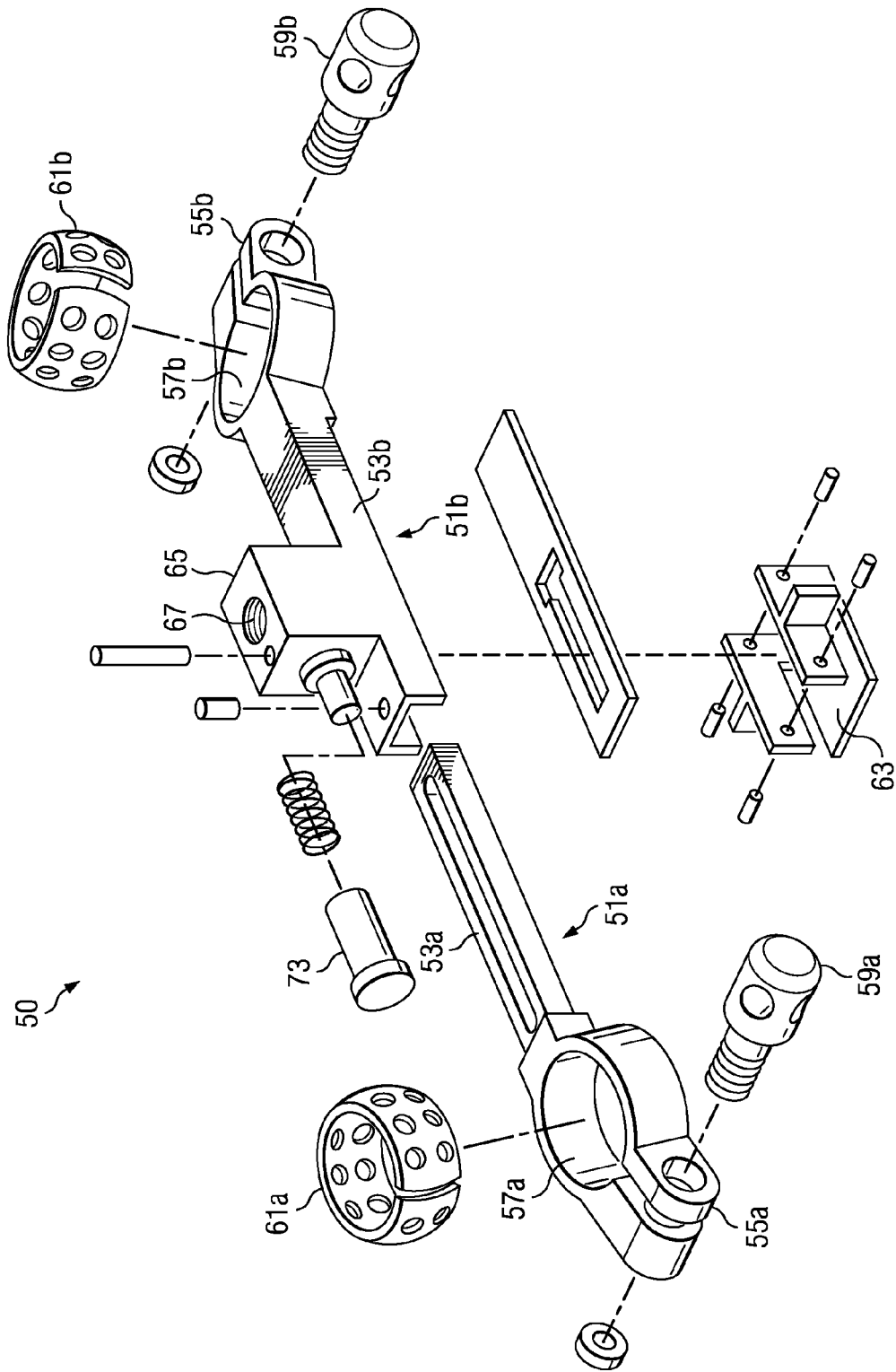
FIG. 2 is an exploded view of an embodiment of a ratcheting connector suitable for use with the disclosed invention.

Referring now to FIG. 2, an exploded view of a first embodiment of the novel ratcheting connector 50 is shown. The ratcheting connector 50 provides a means of connecting pairs of head holders 1 located on a single vertebral body. The ratcheting connector 50 may account for variability in pedicle screw trajectory and effectively distributes rotational forces over two pedicle screws rather than focusing the load on single pedicle screw. Various embodiments of the ratcheting connector 50 further permits one or more of the following benefits: transverse plane adjustment (lock/unlock) for distance between pedicle screws, sagittal plane adjustment (lock/unlock) for variability in trajectory of pedicle screws, simple tightening and locking mechanisms for each plane of adjustment, and a centralized spring loaded receptacle for utilization of rotation handle or, optionally, a flexible arm connector.

Figure 3:
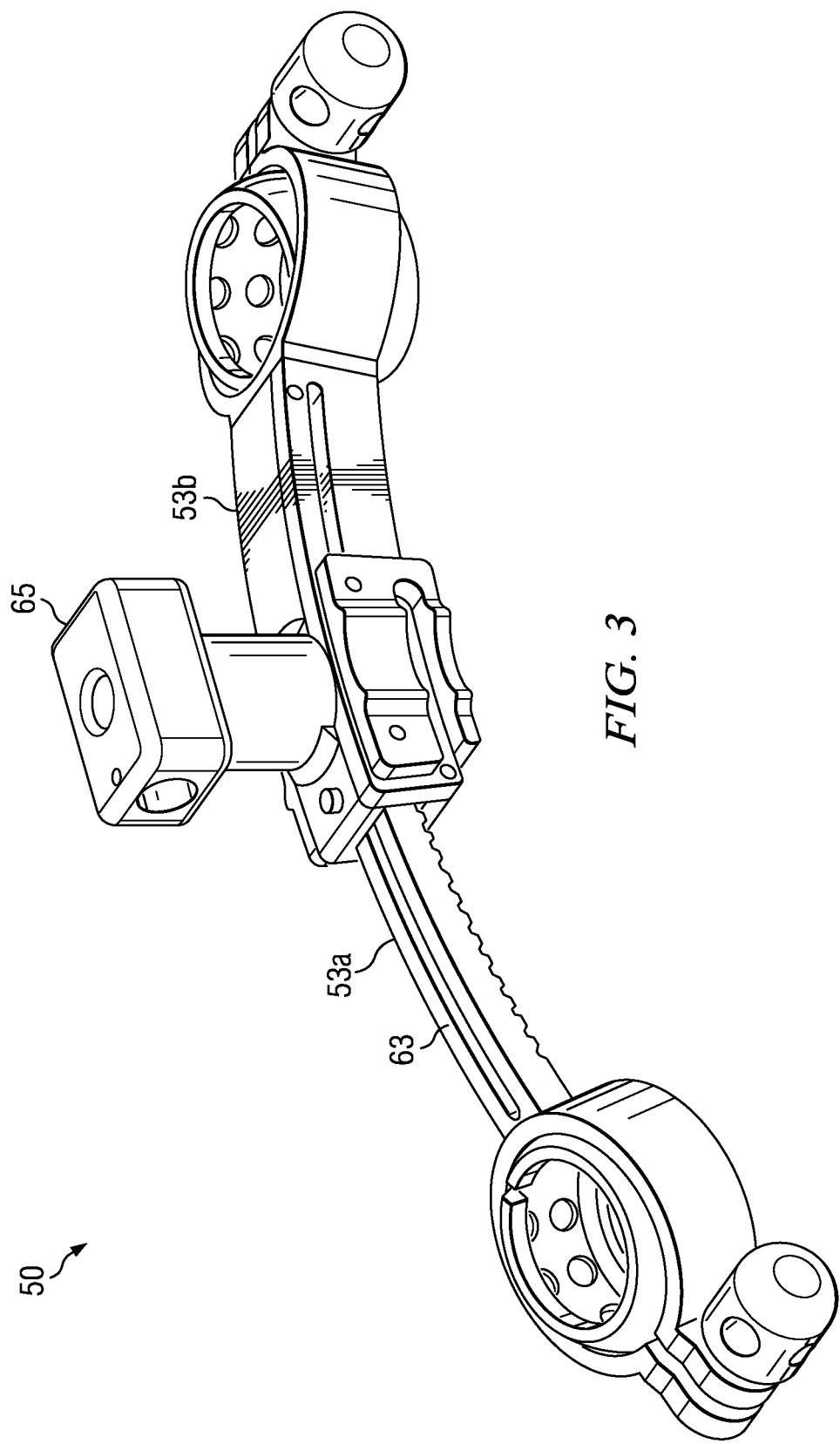
FIG. 3 is a perspective view of an embodiment of a ratcheting connector suitable for use with the disclosed invention.

Referring still to FIG. 2, the first embodiment of the ratcheting connector 50 includes two interconnecting arms 51a and 51b, each arm 51 having a inner sections 53a and 53b and outer sections, 55a and 55b, which can be bent downward. The interconnecting arms 51a and 51b both have generally rectangular cross sections that allow the inner sections 53a and 53b to be slidably connected to each other. Also visible in FIG. 2 is the substantially flat profile of the inner sections 53a and 53b. Each outer section has a circular sleeve, 57a and 57b, the diameter of which is slightly adjustable with a sagittal plane adjustment knob, 59a and 59b. Inside circular sleeves 57a and 57b are rotatable bearings 61a and 61b, respectively. Bearings 61a and 61b have curved outer surfaces allowing them to partially rotate within circular sleeves 57a and 57b. Inner section 53a interconnects with inner section 53b in a manner allowing the distance between circular sleeves 57a and 57b to be adjustable. The distance between circular sleeves 57a and 57b may be locked into place by locking plate 63. Likewise, the distance between 57a and 57b may be allowed to change by unlocking plate 63. Any adjustable interconnecting mechanism may be used. For example, in one embodiment of ratcheting connector 50, flat section 53a has a toothed lower edge 63, as shown in FIG. 3, the teeth of which may engage a pin (not shown) projecting inwardly from an inside surface of flat section 53b. Also visible in FIG. 3 is the substantially curved profiles of the inner sections 53a and 53b.

Embodiments of the ratcheting connector 50 may optionally include a receptacle 67 (as shown in FIGS. 2 and 3). Receptacle 65 includes an opening 67 in its top surface to permit insertion of a rotation handle or flexible arm connector. In some embodiments, receptacle 65 further includes a mechanism to releasably lock the rotation handle or flexible arm connector in opening 67. Such mechanism may be implemented as a spring loaded button 73.

To utilize the ratcheting connector 50, the surgeon sets the transverse plane locking plate 63 the unlocked position. The rotatable bearings 61a and 61b at each end of the ratcheting connector 50 are placed over the proximal ends of two head holders 1 on a single vertebral body. Transverse plane adjustment is achieved by pushing or pulling the rotating clamps in relation to each other. Once the desired configuration has been reached, the plane orientation can be locked by moving the locking plate 63 into the locked position to prevent further movement of the flat sections 53a and 53b. Sagittal plane adjustment can be achieved by rotating the rotatable bearings 61a and 61b to the desired trajectory or angle with respect to sleeves 57a and 57b. Once the desired configuration has been reached, the sagittal plane adjustment knob 59a and 59b can be locked thereby tightening the sleeves 57a and 57b onto rotatable bearings 61a and 61b respectively. The receptacle 65 at the top of the ratcheting connector allows for the utilization of a rotation handle or flex arm connector (as shown in FIG. 5).

To disconnect the ratcheting connector 50 from the head holders 1, the sagittal plane adjustment knobs 59a and 59b are unlocked and the transverse plane locking plate 63 is also unlocked. Once all adjustments have been loosened, the ratcheting connector 50 slips off over the proximal end of each head holder 1.

Figure 4:
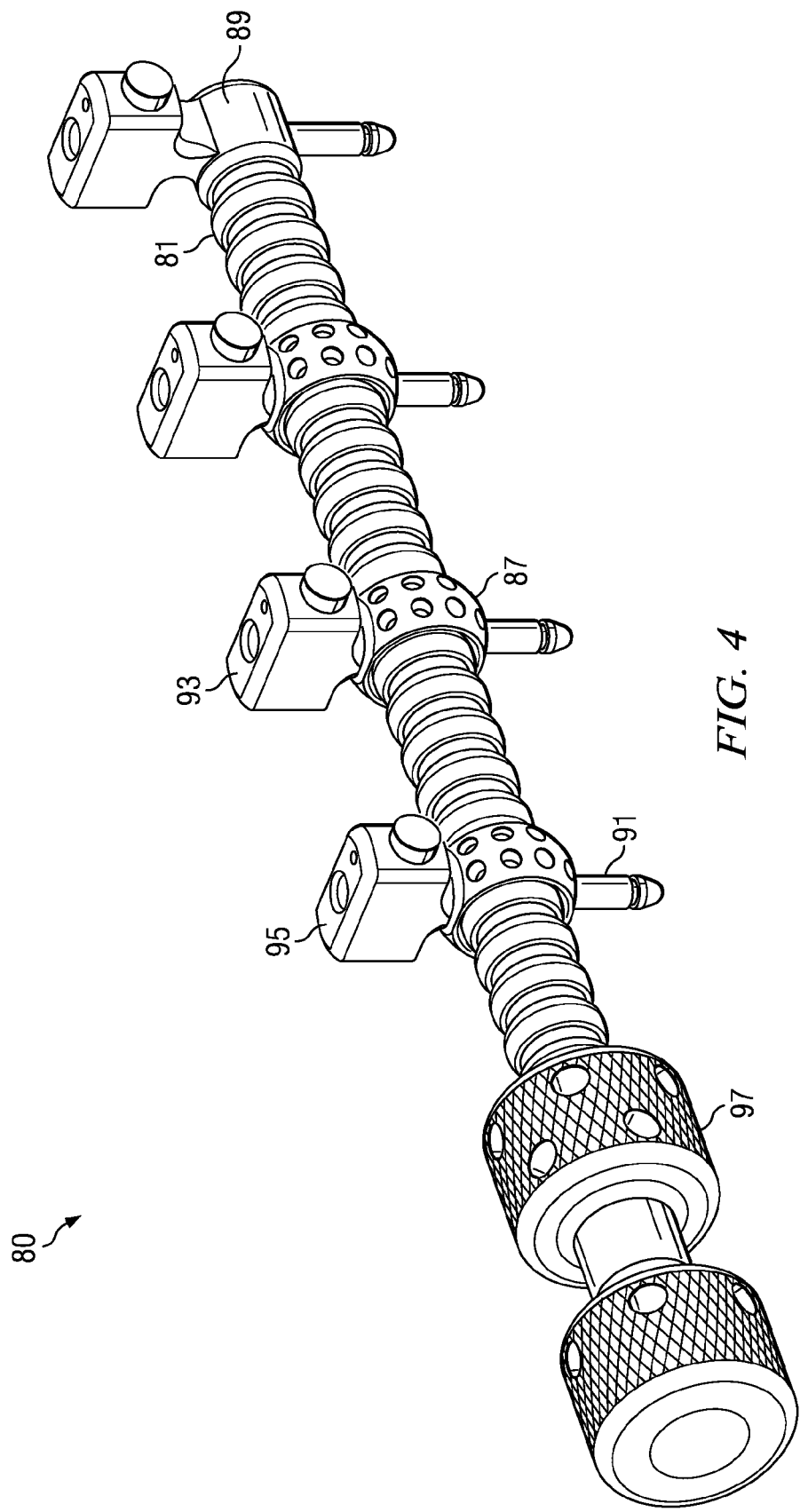
FIG. 4 is a perspective view of an embodiment of a flex arm connector suitable for use with the disclosed invention.

Referring now to FIG. 4, a perspective view of the flex arm connector 80 is shown. Flex arm connector 80 provides a means of connecting a series of ratcheting connectors 50 located on consecutive vertebral bodies. The flex arm connector 80 can account for variability in rotation in consecutive vertebral bodies and effectively distributes rotational forces over multiple vertebral bodies rather than focusing the load on a single vertebral body. Various embodiments of the flex arm connector 80 further permits one or more of the following benefits: sagittal plane adjustment for off axis location of pedicle screws on consecutive vertebral bodies; transverse/ coronal plane adjustment for variance in rotation between consecutive vertebral bodies; simple tightening and locking mechanism for each plane of adjustment; and centralized receptacle for optional utilization of a rotation handle.

Figure 5:
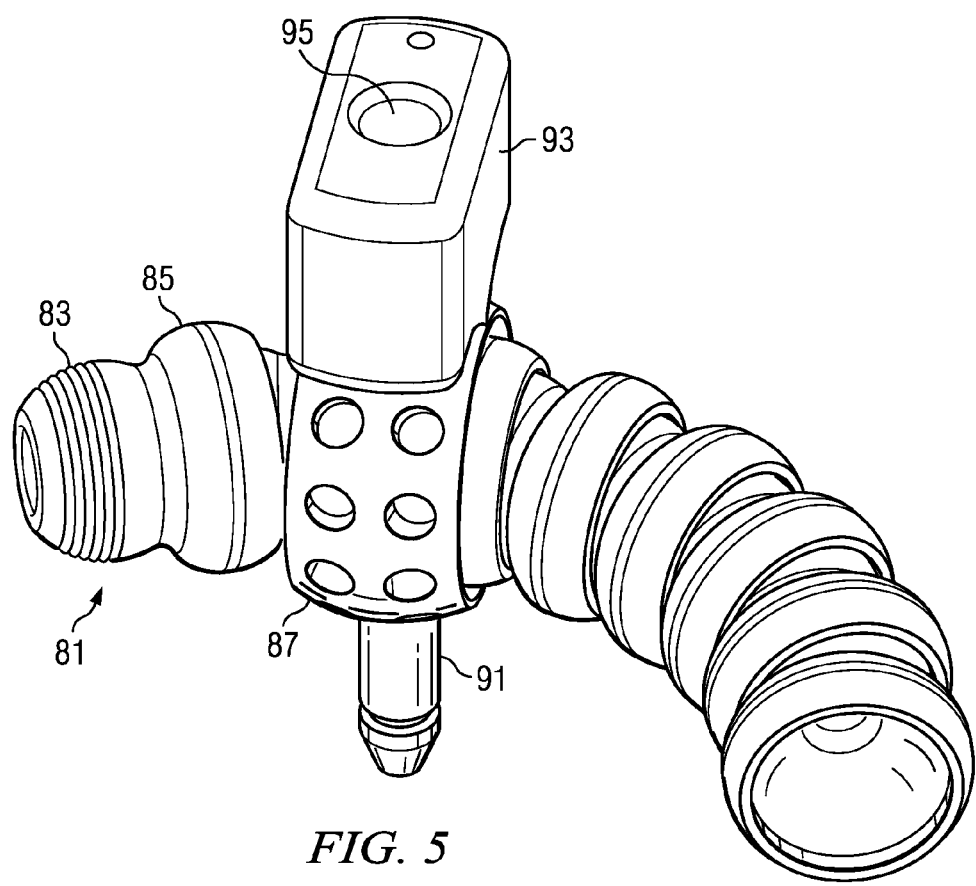
FIG. 5 is a perspective view of a portion of the flex arm connector shown in FIG. 4.

Referring to FIG. 5, a perspective view of a portion of a flex arm connector 80 is shown. In preferred embodiments, the flex arm connector is made of a plurality of nesting cups 81. Each cup includes a male portion 83 and a female portion 85, with the male portion of one nesting cup fitting rotatably within the female portion of a proximate nesting cup. The length of the flex arm connector 80 is adjustable, prior to use, by adding or removing nesting cups 81.

Figure 6:
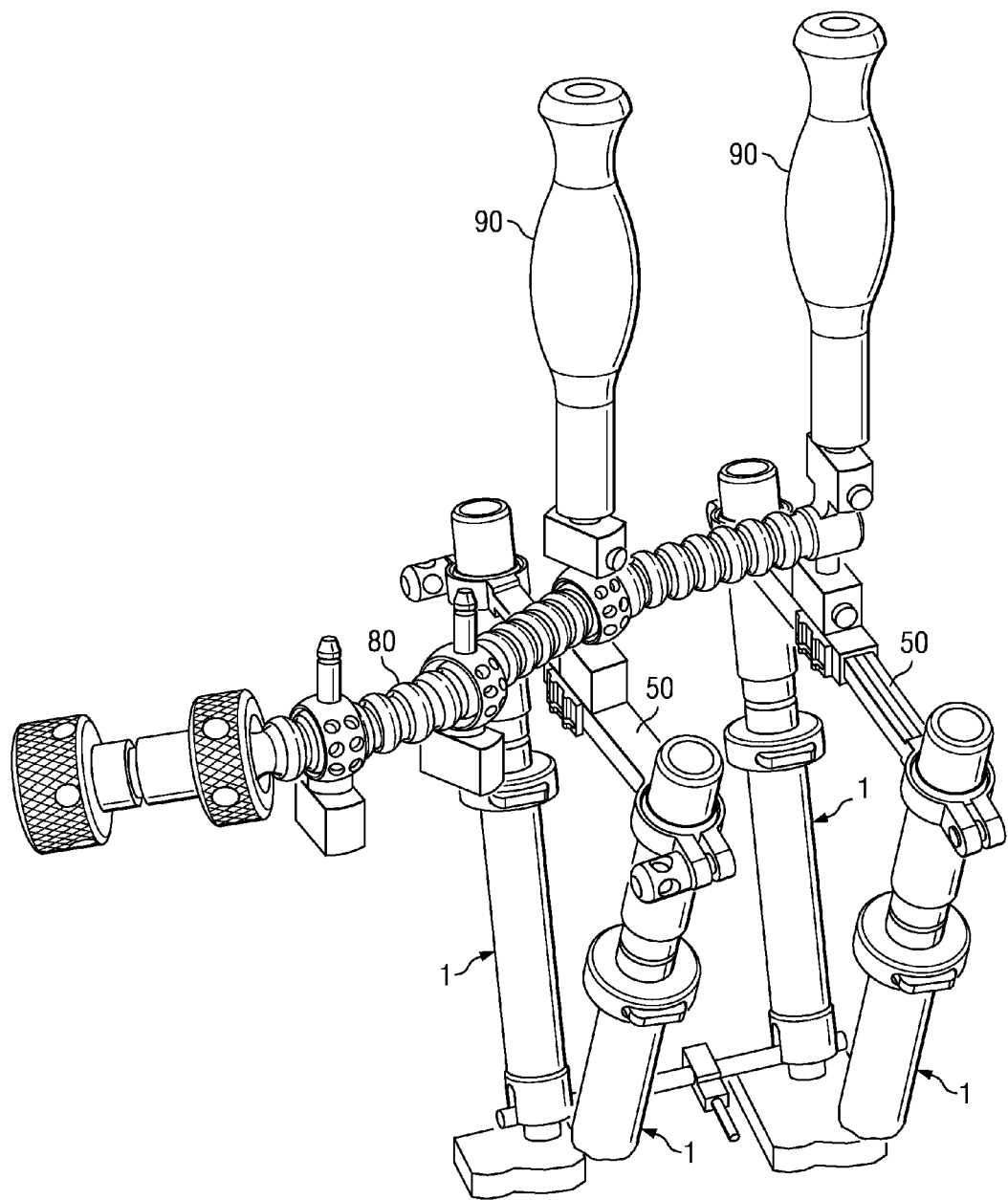
FIG. 6 is a perspective view of an embodiment of a tool set suitable for use with the disclosed invention.

Referring again to FIG. 4, a flex arm connector for use with four ratcheting connectors 50 is shown. At one end of the flex arm connector 80 is a locking mechanism 97, engagement of which causes the flex arm connector 80 to become rigid in the position in which it is placed. Optionally, at an opposite end of the flex arm connector 80 is a terminal sleeve 89. Adjustable sleeves 87 can be placed at desired locations along the flex arm connector 80 and locked into place, by means of, for example, a set screw. Each of adjustable sleeves 87 and terminal sleeve 89 includes a swivel post 93. Swivel posts 93 optionally include a tapered end 91 and means for interlocking, such as ridges and/or grooves, with receptacle opening 67 of FIG. 2. Swivel posts 93 further include rotation handle openings 95 which are configured to accept rotation handles 90 (FIG. 6). In some embodiments of the flex arm connector 80, a rotation handle receptacle 95 is provided that includes an opening to receive a rotation handle.

To utilize the flex arm connector 80, the surgeon inserts the swivel posts 91 into the receptacle opening 67 (FIG. 2) of the ratcheting connectors 50 (See FIG. 6). Sagittal plane adjustment can be achieved by sliding the adjustable sleeves 87 along the axis, or length, of the flex arm connector 80 and inserting swivel posts 91 into the receptacle openings 67 on ratcheting connectors 50 on consecutive vertebral bodies. Sagittal plane adjustment can be achieved using the flexible cable and segments to trace the trajectory of the previously attached ratcheting connectors on consecutive vertebral bodies. The sagittal trajectory can be locked by engaging locking mechanism 97.

To disconnect the flex arm connector 80 from the ratcheting connectors 50, the transverse plane adjustment is unlocked by disengaging locking mechanism 97 so that the flex arm connector is no longer rigid. The swivel posts 91 can then be removed from the receptacle openings 67 of the ratcheting connectors 50. In some embodiments, it may be desirable to disengage any locking mechanism of the receptacle 65.

Referring now to FIG. 6, an embodiment of a tool set of the present invention is shown. As shown in FIG. 6, the tool set includes four head holders 1, two ratcheting connectors 50, and a flex arm connector 80. FIG. 6 further shows rotation handles 90 that interlock with rotation handle openings 95 (FIG. 4).

It will be understood that various embodiments of the invention may include varying numbers of head holders and ratcheting connectors, depending upon the length of spinal adjustment needed. Moreover, it will be understood that a flex arm connector may not be included in all embodiments of the tool set of the present invention. Rather, certain embodiments may include solely head holders and ratcheting connectors and rotation handles.

I claim:
1. A vertebral rotation tool comprising:
   a head holder comprising:
      a handle portion having a generally tubular shape, a distal end and a proximal end;
      an inner sheath having a tubular proximal end and a distal end having two U-shaped cutouts, two arc-shaped head clamp portions adapted to receive a head of a pedicle screw;
      an outer sheath having a distal end and a proximal ring section and a longitudinal axis defined therebetween, the proximal ring section including a locking mechanism that permits the outer sheath to move between and to reside in locked and unlocked positions, wherein the locking mechanism is operable to be depressed substantially perpendicular to the longitudinal axis in the unlocked position, and wherein the tubular proximal end of the inner sheath can be attached to the handle portion and the outer sheath can surround the inner sheath; and a spring adapted to surround the inner sheath and be positioned between a distal edge of the handle portion and a proximal edge of the outer sheath.

2. The vertebral rotation tool of claim 1 wherein the distal end of the inner sheath is adapted to be releasably connected to the head of the pedicle screw by applying an axial force along a longitudinal axis of the head holder.

3. The vertebral rotation tool of claim 2 wherein the distal end of the inner sheath further comprises pins adapted to releasably connect with a mating feature on the head of the pedicle screw.

4. The vertebral rotation tool of claim 2 wherein the distal end of the outer sheath comprises two opposing U-shaped cutouts adapted to receive a rod and the distal end of the inner sheath.

5. The vertebral rotation tool of claim 1 wherein the outer sheath can be placed into the unlocked position by sliding the outer sheath towards the handle portion along a longitudinal axis of the head holder such that the spring biases the outer sheath towards the distal end of the head holder and wherein the outer sheath can be held in the unlocked position by engaging the locking mechanism.

6. The vertebral rotation tool of claim 5 wherein the outer sheath can be moved from the unlocked position to the locked position by releasing the locking mechanism such that the spring moves the outer sheath in a distal direction over the inner sheath.

7. The vertebral rotation tool of claim 1 wherein the locking mechanism comprises a spring-loaded locking ring and a locking button;

wherein the spring-loaded locking ring is adapted to receive the distal end of the handle portion and engage with one of a proximal groove formed on an outer surface of the handle portion or a distal groove formed on the outer surface of the handle portion; and wherein when the spring-loaded locking ring is engaged with the distal groove on the handle portion, the outer sheath is placed in the unlocked position and when the spring-loaded locking ring is engaged with the proximal groove on the handle portion, the outer sheath is placed in the locked position.

8. The vertebral rotation tool of claim 7 wherein the spring-loaded locking ring can be disengaged from the unlocked position by pressing the locking button.

9. The vertebral rotation tool of claim 1 further comprising:
a ratcheting connector comprising:
a first arm comprising a first inner section and a first outer section, the first outer section comprising a first adjustable circular sleeve;
a first rotatable bearing adapted to be rotatably mounted within the first adjustable circular sleeve;
a first mechanism adapted to lock the first adjustable circular sleeve around the first rotatable bearing;
a second arm comprising a second inner section and a second outer section, the second outer section comprising a second adjustable circular sleeve and a receptacle having an opening;
a second rotatable bearing adapted to be rotatably mounted within the second adjustable circular sleeve;
a second mechanism adapted to lock the second adjustable circular sleeve around the second rotatable bearing;
wherein the first and second inner sections are adapted to be slidably connected to each other to permit adjustment of a distance between the first and second adjustable circular sleeves.

10. The vertebral rotation tool of claim 9 wherein the first and second inner sections have substantially rectangular cross-section that can be slidably mounted to each other.

11. The vertebral rotation tool of claim 10 wherein the first and second inner sections have a substantially flat profile.

12. The vertebral rotation tool of claim 10 wherein the first and section inner sections have a substantially curved profile.

13. The vertebral rotation tool of claim 9 wherein a bottom surface of the first inner section comprises a toothed surface and a bottom surface of the second inner section comprises at least one pin adapted to engage with one or more recesses of the toothed surface to lock a position of the first arm with respect to the second arm.

14. The vertebral rotation tool of claim 9 wherein the ratcheting connector further comprises a receptacle placed on an upper surface of the ratcheting connector that can receive and releasably lock an installation tool.

15. The vertebral rotation tool of claim 14, wherein the installation tool is a rotation handle adapted to apply a rotational force to the ratcheting connector.

16. The vertebral rotation tool of claim 14, wherein the installation tool is a flex arm connector comprising:
a plurality of nesting cups, each cup having a female portion and a male portion such that the male portion nests within the female portion, the plurality of nesting cups forming a flexible length;
a mechanism for locking the flex arm connector into a desired configuration attached to one end of the flexible length; and
at least one adjustable sleeve adapted to be slidably mounted on the flexible length, each adjustable sleeve including a mechanism to lock the sleeve at a location on the flexible length, each sleeve further including a swivel post configured to interlock with the receptacle.

17. The vertebral rotation tool of claim 16 wherein the at least one adjustable sleeve further comprises a receptacle having an opening, the receptacle located opposite the swivel post.

18. A vertebral rotation tool comprising:
a head holder comprising:
a handle portion having a generally tubular shape, a distal end and a proximal end;
an inner sheath having a tubular proximal end and a distal end having two U-shaped cutouts, two arc-shaped head clamp portions adapted to receive a head of a pedicle screw;
an outer sheath having a distal end and a proximal ring section and a longitudinal axis defined therebetween, the proximal ring section including a locking mechanism that permits the outer sheath to move between and to reside in locked and unlocked positions, wherein the locking mechanism is operable to be depressed substantially perpendicular to the longitudinal axis in the unlocked position, and wherein the tubular proximal end of the inner sheath can be attached to the handle portion and the outer sheath can surround the inner sheath;

wherein the distal end of the inner sheath is adapted to be releasably connected to the head of the pedicle screw by applying an axial force along a longitudinal axis of the head holder; and a ratcheting connector comprising:
- a first arm comprising a first inner section and a first outer section, the first outer section comprising a first adjustable circular sleeve;
- a first rotatable bearing adapted to be rotatably mounted within the first adjustable circular sleeve;
- a first mechanism adapted to lock the first adjustable circular sleeve around the first rotatable bearing;
- a second arm comprising a second inner section and a second outer section, the second outer section comprising a second adjustable circular sleeve and a receptacle having an opening;
- a second rotatable bearing adapted to be rotatably mounted within the second adjustable circular sleeve;
- a second mechanism adapted to lock the second adjustable circular sleeve around the second rotatable bearing;
- wherein the first and second inner sections are adapted to be slidably connected to each other to permit adjustment of a distance between the first and second adjustable circular sleeves; and wherein the ratcheting connector further comprises a receptacle placed on an upper surface of the ratcheting connector that can receive and releasably lock an installation tool.

19. The vertebral rotation tool of claim 18, wherein the installation tool is a rotation handle adapted to apply a rotational force to the ratcheting connector.

20. The vertebral rotation tool of claim 18, wherein the installation tool is a flex arm connector comprising:
- a plurality of nesting cups, each cup having a female portion and a male portion such that the male portion nests within the female portion, the plurality of nesting cups forming a flexible length;
- a mechanism for locking the flex arm connector into a desired configuration attached to one end of the flexible length; and
- at least one adjustable sleeve adapted to be slidably mounted on the flexible length, each adjustable sleeve including a mechanism to lock the sleeve at a location on the flexible length, each sleeve further including a swivel post configured to interlock with the receptacle.

* * * * *